United States Patent [19]

Ohme et al.

[11] 4,410,709
[45] Oct. 18, 1983

[54] SULFOBETAINES

[75] Inventors: Roland Ohme; Detlef Ballschuh; Jochen Rusche; Horst Seibt; Kristina Geneis; Günter Kretzschmar, all of Berlin, German Democratic Rep.

[73] Assignee: Akademie der Wissenschaften der DDR, Berlin, German Democratic Rep.

[21] Appl. No.: 281,432

[22] Filed: Jul. 8, 1981

[30] Foreign Application Priority Data

Jul. 11, 1980 [DD] German Democratic Rep. ... 222563

[51] Int. Cl.$^3$ .......................................... C07D 207/08
[52] U.S. Cl. ................................ 548/570; 260/245.7; 544/71; 548/147; 548/408; 548/409
[58] Field of Search ........................ 548/570, 408, 409

[56] References Cited

U.S. PATENT DOCUMENTS 3,644,343  2/1972  Manning ......................... 548/409 X Primary Examiner—Richard Raymond
Attorney, Agent, or Firm—Jordan and Hamburg

[57] ABSTRACT

The invention relates to new sulfobetaines and a process for the manufacture of cyclic sulfobetaines of a substituted 4-sulfomethyl-pyrrolidinium betaine type.

Diallylammonium combinations are converted with salts of sulfurous acid, under good mixing and mild reaction conditions, in the presence of catalytic acting transition metallic ions of the first, fifth, seventh or eighth secondary groups of the Period Table and initiators at pH 2–9. The process is technologically easily carried out, requires only little energy, while the combinations according to this invention can be selectively manufactured with a nearly quantitative yield. The fact that no carcinogenic alkylates are employed, technical chemicals and tap water may be used, and hardly any by-products are formed, may be regarded as further advantages of this process.

The substances can be used for multiple purposes, for instance as conductive coating and antistatic materials. Moreover, long-chained substituted compounds have valuable surface tension qualities and an excellent cleaning power at low temperatures.

10 Claims, No Drawings

SULFOBETAINES

BACKGROUND OF THE INVENTION AND PRIOR ART STATEMENT

This invention covers new sulfobetaines as well as a process for the manufacture of these sulfobetaines of the general formula I,

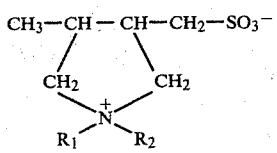

in which $R_1$ represents hydrogen, straight-chained or branched alkyl groups of $C_1$ to $C_{22}$ or benzyl, and $R_2$ represents straight-chained or branched alkyl groups of the same chain length range as indicated for $R_1$, wherein $R_1$ and $R_2$ may be equivalent or different and may form a heterocyclic ring together with the nitrogen atom to which they are bound, optionally through oxygen.

Internal salts of the general formula I increase the conductivity of solutions and may be employed as conductible coating and antistatic materials. Moreover, if $R_1$ represents straight-chained or branched alkyl groups with 6–22 C-atoms, these sulfobetaines will have valuable surface tension qualities; they may then be employed as thermostable antistatic agents for synthetic plastic materials and as coating agents for all kinds of surfaces, for instance in sheets and woven fabrics. They may be employed as emulsifiers and flotation agents, as dyeing agents and as a component of laundry and cleaning agents at low temperatures for energy-saving laundering processes because of their excellent cleaning power. Some representatives of this new class of substances have exceptional foaming ability so that they are suitable for the manufacture of dry cleaning foams. These sulfobetaines are easily mixed with other surface-active substances, for instance with nonionics. Their excellent solubility in non-aqueous systems opens possibilities of application in the manufacture of stable OW (oil-in-water) and WO (water-in-oil)-emulsions or—in combination with biologically active substances—for use in agents with improved operational value, for instance for improved plant protection agents. They may further be employed as additives in oils.

Sulfobetaines are known in which the cation is not a part of the ring system. These are preferably obtained by alkylation of tert. amines with derivatives of hydroxyalkane sulfonic acids (Parris, Weil, Linfield, J. Amer. Oil Chem. Soc. 53 (1976) 97; DD-PS 139719). Above all, however, the propane sulfone serves to introduce a sulfopropyl group (DE-AS 2431031; DE-AS 2409412). Besides the disadvantageous multiple stages of this process, a further disadvantage of the principally used processes involving propane sulfone is that propane sulfone has been recognized as constituting a dangerous carcinogen and, because of this, it was necessary to deploy precautionary measures, incurring considerable expenses (H. Druckrey and colleagues, Z. Krebsforschung 75 (1970) 69; Reg. of Toxic Effects of Chem. Subst., Nat. Inst. for Occupational Safety and Health, Md., U.S. 1975). Further, hydrogen sulfite addition to trialkylallylammonium salts for the synthesis of sulfobetaines has been proposed by Linfield et al. (J. Amer. Oil Chem. Soc. 53 (1976) 60; 55 (1978) 87). The disadvantages of this process are that the products obtained are of little uniformity when air is excluded, and while working under pressure with long reaction times.

DE-OS 2331515 comprises a process for the addition of hydrogen sulfite radicals to unsubstituted olefins, in which transition metals from the first, seventh and eighth secondary group of the Periodic Table are used as catalysts.

However, the olefins used in that process cannot be compared with the dialkyldiallylammonium compounds of the present invention since they are unsubstituted and have isolated double bonds. Thus they differ considerably regarding their electron configuration and reactivity, from the diallylammonium compounds used in the present invention.

It is the object of this invention to manufacture the sulfobetaines of formula I. The process is to be carried out under mild reaction conditions. It should attain a possible quantitative corrosion with short reaction times, high selectivity, and should keep the level of organic waste products at a minimum through the addition of approximate stoichiometric quantities of the reaction partners.

SUMMARY OF THE INVENTION

This object is attained through the novel sulfobetaines of the general formula I,

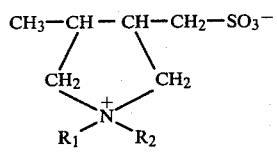

in which $R_1$ represents hydrogen, straight-chained or branched alkyl groups with $C_1$ to $C_{22}$ or a benzyl group, and $R_2$ represents straight-chained or branched alkyl groups with $C_1$ to $C_{22}$, wherein the groups $R_1$ and $R_2$ may be equivalent or different or, together form a heterocyclic ring with the nitrogen atom to which they are bound, possibly through oxygen.

DETAILED DESCRIPTION OF PREFERRED EMBODIMENTS

According to the present invention, diallylammonium compounds of the formula II

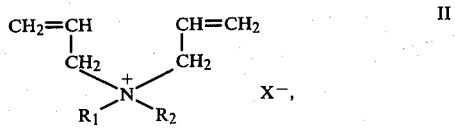

wherein $R_1$ and $R_2$ have the same meaning as in formula I and X is an anion, are reacted in solution with a salt of sulfurous acid in the presence of ions of the transition metals of the first, fifth, seventh or eighth secondary group of the Periodic Table, plus initiators.

This conversion is effected under good intermixing at a temperature ranging from 10°–80° C. and a pH-value of 2–9. It is advantageous to make the conversion in an aqueous or alcoholic solution or in a mixture of alcohol and water. Suitable alcohols are isopropanol, tert. butanol, ethanol or mixtures of such alcohols with water.

The reaction requires the presence of initiators, preferably oxygen in air. Diallylammonium compounds may be used which have halide, hydrogen sulfite, methosulfate, hydrogen sulfate or an equivalent sulfite or sulfate as their anion. Besides water, alcohols or alcohol-water mixtures are also suitable as a solvent for the diallylammonium compounds. Ions of the transition metals, such as $Cu^{++}$, $V^{5+}$, $Mn^{4+}$, $Fe^{+++}$, $Co^{++}$ or $Ni^{++}$ are especially suitable.

The catalyst metals may be added in the form of salts or oxides or in contact with metallic Cu, Fe, Ni or alloys with the introduction of air into the reaction medium.

Sulfobetaine formation occurs with technically useful speed preferably in the pH-range 4–8.

The operation is usually performed at 20°–50° C. Conversion is effected at higher temperatures (up to 80° C.) in those cases where extremely low solubility of the diallyl compounds is required.

Surprisingly, it was found that the noted diallylammonium compounds take up hydrogen sulfite on the one hand, and, on the other hand, a simultaneous cyclization takes place. 1.7 hydrogen sulfite is added to the diallylammonium system herein, while, with the new attachment of the C—S— and the C—H—bond at the same time, a ring-closing C—C—attachment between the C-2 and 6 atoms unexpectedly still occurs.

The process of this invention differs substantially from previously described olefin-sulfite-addition processes (for instance in DE-OS 2331515), in which hydrogen sulfite is added to proximate C=C—double bonds, 1. by the introduction of substances with a diallylammonium structure which, in a comparison with previously used olefins, have a considerably different electron configuration and reactivity, and
2. by the introduction of a sulfonic acid group in which a sulfocyclization occurs.

Although the possibility of using allylammonium salts in sulfite radical addition reactions under substantially more drastic conditions (pressure, higher temperature, long reaction times) was made known from the J. Amer. Oil Chem. Soc. 53 (1976), 60, it was not expected that a 1.7 addition and, additionally, a cyclization with hydrogen sulfite would occur in diallylammonium compounds. The efficacy and pH-dependency of the homogeneous catalysis exhibits a behavior similar to that known for sulfite oxidation in aqueous solution (A. Huss, J. Amer. Chem. Soc. 100, (19) 6252 (1978)). For this reason, it is most probable that the sulfite anion radical is responsible for triggering such reaction.

Exceptionally low catalyzing quantities are necessary. Since the sulfite oxidation evidently is already catalyzed by so small a quantity of $10^{-8}$ gram atom/liter of a transition metal, concentrations of $10^{-6}$ to $10^{-4}$ gram atom/liter are fully sufficient for preparation purposes. In most cases, when working with tap water and/or technical chemicals as well as when utilizing metallic apparatuses and equipment, sufficient quantities of $Fe^{+++}$ and other heavy metals are present to trigger the reaction. However, it is possible to exclude homogeneous catalysis by blocking the heavy metals with sulfide or mercaptide or through formation of strong complexes (ethylenediaminetetra-acetic acid).

The required pH-range can be maintained through buffering or the introduction of sulfur dioxide into the reaction solution. The reaction may also be effected under pressure in this case, if convenient. It will be advantageous to effect buffering by a mixture of alkali- or ammonium-hydrogen sulfite with alkali- or ammonium sulfite. sulfite, the loss that occurs by the secondary reaction in sulfate formation will also be compensated.

The consumption of $HSO_3^-$-ions occurring in the course of the reaction results in an increase of the pH value. The oxidation of $HSO_3^-$ into $HSO_4^-$, however, produces a pH decrease so that the buffering capacity of the reaction mixture may be restricted. Sulfobetaine formation occurs in a temperature range from 20°–40° C. in brief reaction time (15–60 minutes), in mostly quantitative yields, if the solution of the diallyl compound and the hydrogen sulfite too are introduced at the same time into the reaction mixture while the pH value remains constant to prevent cyclopolymerization. Air or oxygen are introduced during the reaction and distributed throughout the reaction mixture by heavy stirring. The exclusion of air will stop the reaction.

Water is the preferred solvent. It is possible to dissolve a mixture of water and alcohol, when required by the solubility characteristics of the substrates, wherein 2-propanol has been found to be an especially good solvent. A mixture of water and isopropanol in the ratio 30:70 will be sufficient to dissolve the sulfite; alcohol, especially isopropanol, are suitable anti-foaming agents.

The diallylammonium salts required as starting substances can be obtained in a simple manner either from amines through allylation or from diallylamines through alkylation, wherein, in many cases, it is possible to forgo isolation and purification; often the cyclizing sulfonation is obtained without isolating intermediate products.

It is desirable to gradually add the diallylammonium compound and the solution of salts of sulfurous or disulfurous acid to the reaction mixture at the same time. In order to prevent adding an inordinate excess of sulfite as buffering agent, it is also possible to operate under pH control wherein it will be advisable to employ a small quantity of neutral sulfite at the beginning of the trickling.

Instead of oxygen in air, the reaction may also be started with traditional radical initiators, for instance by the addition of ammonium persulfate, nitrates, nitrites, hydrogen peroxide or by organic peroxides and hydroperoxides. However, this operating procedure, as a rule, does not result in greater advantages because of the higher expenditures; however, the use of such initiators may be advantageous on working with foaming reaction mixtures. Also, the simultaneous use of radical initiators and limited oxygen quantities may be advantageous, if foaming substrates without anti-foaming additives are to be processed. Initiation by UV or gamma rays is also possible.

The advantages of the novel sulfobetaines and the process of this invention comprise
mild reaction conditions can be employed;
the reaction times are short;
energy requirements are low;
it is possible to use starting products of technical purity;
selectivity in the reaction is high;
the yields are very high;
it is possible to manufacture previously unknown substances and
multiple possibilities exist for application for the sulfobetaines that can be manufactured.

EXAMPLES

Example 1a 1,1,3-trimethyl-4-sulfomethyl-pyrrolidinium-betaine;
$R_1 = R_2 = CH_3$ in the general formula.

Dimethyldiallylammonium chloride was obtained through the reaction of dimethylamine with allylchloride in the presence of a solution of caustic soda. The following solutions are prepared:

1. 307 g (1 mol) 52.6% aqueous technical dimethyldiallylammonium chloride solution with 4.85% NaCl content are diluted in tap water ($10^{-6}$ gram atom $Fe^{+++}$/liter) to form a 450 ml solution.
2. 95 g (0.5 mol) $Na_2S_2O_5$ (sodium metabisulfite) and 63 g (0.5 mol) sodium sulfite $Na_2SO_3$ are diluted in tap water to form a 450 ml solution.
3. 12.6 g (0.1 mol) sodium sulfite $Na_2SO_3$ are diluted in tap water to form a 600 ml solution.

Solution 3 is introduced in a sulfonation flask provided with a stirrer, dripping funnel, gas-inlet tube and thermometer. Solutions 1 and 2 are then simultaneously dripped into the flask for a duration of 65 minutes and beginning with a temperature of 18° C. Air is introduced during the dripping, and a white, milky emulsion of small air bubbles is produced with the heavy stirring, this being an important prerequisite for rapid conversion. The temperature of the reaction mixture increases to 44.6° C. during the entire period of the dripping time, the pH value remaining between 8 and 7 during the whole duration of the reaction. After another 10 minutes, the temperature decreases to 43° C., this signalling the end of the reaction. Conversion at this time is quantitative, as can be detected by NMR spectroscopy in the dwindling of the allyl proton signals.

Iodometric back-titration of the unreacted sulfite portions results in 0.47 mol unreacted $SO_3^{--}$.

After the reaction solution is concentrated for drying, a colorless mixture of sulfobetaine with sodium sulfite, sodium sulfate and sodium chloride is obtained, from which sulfobetaine cannot be extracted with ethanol; however, a reduction of the neutral salts can be obtained by concentration, separation from the precipitated salts and, further concentrating the sulfobetaine solution by drying or precipitation with ethanol. The sulfobetaine recrystallizes into shiny little flakes.

Melting point: decomposition starting at 275° C.

The product shows the following $^{13}C$-NMR spectrum ($D_2O$, external standard TMS):

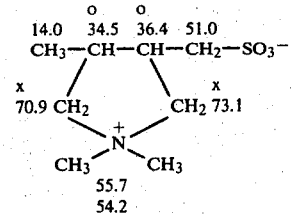

The figures indicated with the atomic symbols correspond to the chemical displacements for the cis-form in ppm.

x; o: chemical displacements may be interchanged.

The N-$CH_3$ groups are not equivalent.

H-NMR spectrum in $D_2O$; internal standard sodium-trimethylsilylpropane sulfonate (TMSPS). Chemical displacement, $\tau$ values in ppm:

| d 8.90 | J = 6.5 Hz, | ring - $CH_3$ |
|---|---|---|
| s 6.69, s 6.78 | | N—$CH_3$, non-equivalent |
| m 5.8–7.2 | | ring protons and —$CH_2$—$SO_3^-$ |

Example 1b 1,1,3-trimethyl-4-sulfomethyl-pyrrolidinium-betaine:

Operating procedure with molar introduction of hydrogen sulfite, 0.1 mol sodium sulfite in an operating volume of 1000 ml/mol: A solution of 0.756 kg (3 mol) $Na_2SO_3 \cdot 7H_2O$ diluted in 10.8 l tap water is poured into a vessel provided with a stirrer, reflux condenser and air-inlet tube. 9.21 kg (30 mol) 52.6% aqueous solution of dimethyl-diallyl-ammonium chloride are simultaneously added drop by drop to this solution, to which 630 g water have been added (totalling 9.15 l solution) and 9.15 l of a solution of 2.85 kg $Na_2S_2O_5$ (15 mol) in tap water. A strong current of air is conducted during this drop-wise addition into the reaction solution, which is strongly stirred in order to achieve a finest possible distribution of the oxygen. Starting with a temperature of 25° C., the trickling is effected for two hours, achieving a final temperature of 52° C. After a further reaction time of 15 minutes, the lowering of the temperature indicates the end of the conversion. Conversion at this point is quantitative, as evidenced by $^1H$-NMR spectroscopy with the disappearance of the allyl proton signals.

The cyclopolymer is derived as secondary product by this operating procedure in a quantity of 6.6% of theoretical; recognizable by a multiplette of the $^1H$-NMR spectrum at $\tau = 8.25$–8.72 ppm.

Example 1c 1,1,3-trimethyl-4-sulfomethyl-pyrrolidinium-betaine;
$R_1 = R_2 = CH_3$ in the general formula I, triggering of reaction through redoxycatalysis:

12.6 g (0.1 mol) $Na_2SO_3$ and 3.8 g (0.02 mol) $Na_2S_2O_5$ are dissolved in 1600 ml tap water in a sulfonation flask provided with a stirrer, thermometer and gas-inlet tube. Then two aqueous solutions, each of 400 ml, are prepared; one from 307.4 g (1 mol) 52.6% technical dimethyldiallylammonium chloride solution, 4.56 g (0.02 mol) ammoniumperoxydisulfate and tap water and the other one from 95 g (0.5 mol) $Na_2S_2O_5$, 63 g (0.5 mol) $Na_2SO_3$ and tap water.

Under stirring and simultaneous introduction of nitrogen, the prepared solutions are added, drop by drop, from two dripping funnels in the period of 65 minutes, during which the temperature of the reaction mixture rises from 22° C. to 35.5° C. During the conversion, the pH value will remain in the 7 range. A sample taken immediately after the conversion exhibited quantitative conversion ($^1H$-NMR spectrum); the spectrum was identical with that for a product in Example 1a.

Example 2a 1,3-dimethyl-4-sulfomethyl-pyrrolidinium-betaine;
$R_1 = CH_3$, $R_2 = H$ in the general formula I 1.26 g (0.01 mol) $Na_2SO_3$ are dissolved in 60 ml tap water in a sulfonation flask provided with a stirrer, gas-inlet tube and thermometer. With vigorous stirring and the simultaneous introduction of air, a solution of 9.5 g (0.05 mol) $Na_2S_2O_3$ and 6.3 g (0.05 mol) $Na_2SO_3$, totalling 45 ml of solution, as well as a solution of 14.75 g (0.1 mol) methyldiallylamino-hydrochloride in 45 ml tap water, are dripped out from two dripping funnels in the course of 16 minutes, wherein the temperature of the reaction mixture rises from 20° to 26° C. The lowering of the temperature will indicate the end of the reaction. During conversion the pH value is maintained between 8 and 7. Conversion at the time of the lowering of the temperature is quantitative as can be demonstrated by $^1$H-NMR spectroscopy (disappearance of the allyl protons).

Upon concentration of the solution together with the neutral salts, the substance crystallizes into colorless crystals which are not soluble in ethanol.

$^1$H-NMR spectrum in $D_2O$; inner standard sodium-trimethylsilylpropane sulfonate (TMSPS). Chemical displacement, $\tau$ values in ppm:

| | | |
|---|---|---|
| d 8.97 | J = 7 Hz | ring - CH$_3$ |
| s 7.04 | | N—CH$_3$ |
| m 5.9–7.5 | | ring protons and —CH$_2$—SO$_3^-$ |

Example 2b

One proceeds as described in Example 2a, but dissolves the starting products in distilled water, adding 0.375 mg CuSO$_4$.5H$_2$O ($10^{-5}$ gram atoms/l) as a catalyst. Quantitative conversion is obtained by the same reaction process. The product exhibits the following $^{13}$C-NMR spectrum (in $D_2O$, external standard TMS):

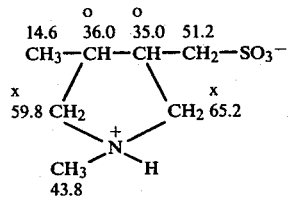

The figures indicated for the atomic symbols correspond to chemical displacements for the cis form in ppm: x; o: chemical displacements may be interchanged.

Example 3

1 Benzyl-3-methyl-4-sulfomethyl-pyrrolidinium betaine; $R_1=C_6H_5CH_2$—, $R_2=H$ in the general formula I.

The same procedure as in Example 2 is used, using 22.4 g (0.1 mol) benzyl-diallylamine hydrochloride for the diallylammonium compound. Full conversion can be established by NMR spectroscopy. The product exhibits following proton signals ($\tau$ values) in $D_2O$ (external standard TMS):

| | |
|---|---|
| m 6.3–7.2 | ring protons, CH$_2$—SO$_3^-$ |
| s 5.66 | phenyl-CH$_2$— |
| s 2.5 | C$_6$H$_5$— |
| d 9.045 | J = 7 Hz ring - CH$_3$ |

Example 4

1,3-dimethyl-1-octyl-4-sulfomethyl-pyrrolidinium betaine; $R_1=CH_3$; $R_2=C_8H_{17}$ in the general formula I Methyl-n-octyl-diallylammoniumbromide was produced by reacting methyldiallylamine with n-octylbromide. 2.52 g (0.02 mol) sodium sulfite as well as 14 mg ($5 \cdot 10^{-5}$ mol/l) FeSO$_4$.7H$_2$O as catalyst are dissolved in 300 ml distilled water in a beaker with a stirrer, thermometer and air-inlet tube. Two solutions of 370 ml each are then prepared with distilled water. One is obtained from 19 g (0.1 mol) sodium metabisulfite and 12.6 g sodium sulfite (0.1 mol); the other one from 60.8 g (0.2 mol) methyl-n-octyl-diallyl-ammonium bromide. Under strong stirring and simultaneous introduction of oxygen in air, one adds the prepared solutions, drop by drop, from a dripping funnel in the course of 50 minutes, wherein the temperature of the reaction mixture increases from 18° to 25.5° C. During conversion, the pH value will remain in the 7 range. After another 10 minutes, the temperature of the reaction will fall. Conversion is already quantitative at this point ($^1$H-NMR). Evaporation follows, after which the sulfobetaine is extracted from the solid salt cake with ethanol. Colorless crystals with a melting point of 132° C. (decomposition) are obtained through re-crystallization of the extracted product with ethanol.

Example 5

1,3-dimethyl-1-decyl-4-sulfomethyl-pyrrolidinum-betaine; $R_1=CH_3$; $R_2=C_{10}H_{21}$ in the general formula I Methyl-n-decyl-diallylammonium bromide was produced by reacting methyldiallylamine with decylbromide. The procedure is the same as described in Example 4, however using 8.7 mg ($10^{-4}$ mol/liter) manganese dioxide as a catalyst and 66.4 g (0.2 mol) methyl-n-decyl-diallylammonium bromide as the diallylammonium compound. The temperature of the reaction mixture increased during the 50 minutes of dripping the reaction partners from 18° to 25.7° C. Work up proceeds as in Example 4. Conversion is quantitative. Melting point: 121° C., colorless crystals from ethanol.

Example 6

1,3-dimethyl-1-dodecyl-4-sulfomethyl-pyrrolidinium-betaine; $R_1=CH_3$; $R_2=C_{12}H_{25}$ in the general formula I Methyl-n-dodecyl-diallylammonium bromide was obtained by reacting methyldiallylamine and dodecylbromide. The procedure is the same as described in Example 4, but using 14 mg ($5 \cdot 10^{-5}$ mol/liter) CoSO$_4$.7-H$_2$O as a catalyst and 72.0 g (0.2 mol) methyl-n-dodecyldiallylammonium bromide as the diallylammonium compound. The temperature of the reaction mixture increases during the 50 minutes of the dripping from 21° to 29° C., wherein isopropanol is occasionlly added to check foaming. Further work up proceeds as described in Example 4. Conversion is quantitative; colorless crystals are obtained from ethanol, melting point: decomposition from 118° C. $^{13}$C-NMR spectrum (in DMSO$_{D6}$), indications as above

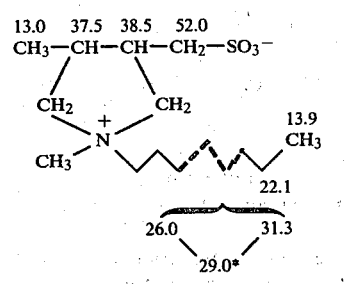

\* most intensive peak
peaks not attributed: 41.7; 40.6; 39.6;

Example 7

1,3-dimethyl-1-tetradecyl-4-sulfomethyl-pyrrolidinium betaine; $R_1=CH_3$, $R_2=C_{14}H_{29}$-in the general formula I Methyl-n-tetradecyl-diallyl-ammonium bromide was produced by reacting methyldiallylamine with n-tetradecylbromide, 3.78 g $Na_2SO_3$ (0.03 mol) are dissolved in 400 ml tap water in a beaker provided with a stirrer, air-inlet tube and thermometer. A solution of 28.5 g $Na_2S_2O_5$ and 18.9 g $Na_2SO_3$ (each 0.15 mol) with water filled up to 400 ml, is simultaneously added, drop by drop, to this solution, as well as a solution of 116.4 g (0.3 mol) of the ammonium salt, dissolved in water to give a 400 ml solution. Air is introduced during the dripping, the solution then is agitated in order to obtain the finest possible distribution of the oxygen. Foam formation can be checked by adding, for instance, isopropanol, if the reaction mixture foams too strongly here. The temperature is increased by 10° C. during approximately 2 hours of dripping. Iodometric back-titration of the unreacted sulfite part yields 60 mmol of unreacted $SO_3$. Conversion is quantitative, as ascertained through $^1H$-NMR spectroscopy. The mixture is then evaporated and the sulfobetaine extracted by ethanol from the reaction product. The colorless crystals of a 126° C. melting point are obtained (decomposition) through recrystallization of the raw product from ethanol. The product exhibits the following $^{13}C$-resonance spectrum ($D_2O$; external standard TMS). The figures indicated next to the symbols correspond to the chemical displacements in ppm:

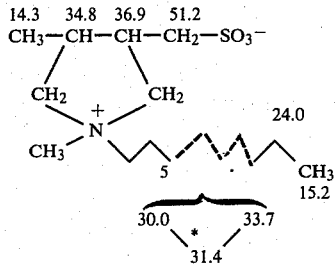

\* most intensive peak
not attributable peaks: 71.6; 69.7; 53.1; 27.7.

Example 8

1,3-dimethyl-1-hexadecyl-4-sulfomethyl-pyrrolidinium betaine; $R_1=CH_3$; $R_2=C_{16}H_{33}$ in the general formula I, was produced by reacting methyl-n-hexadecyldiallylammonium bromide by the process described in Example 7. Colorless crystals were extracted from ethanol, melting point 129° C. (decomposition).

Example 9

1,3-dimethyl-1-octadecyl-4-sulfomethyl-pyrrolidinium betaine; $R_1=CH_3$; $R_2=C_{18}H_{37}$ in the general formula I Methyl-n-octadecyl-diallylammonium bromide was produced by reacting methyldiallylamine with n-octadecylbromide. 1.26 g (0.01 mol) sodium sulfite are dissolved in 300 ml tap water in a sulfonation flask equipped with a stirrer, gas-inlet tube and thermometer and heated at 30° C. Then two aqueous solutions of 200 ml each are prepared. The first is prepared from 9.5 g (0.05 mol) sodium metabisulfite, 6.3 g (0.05 mol) sodium sulfite; the other one from 44.44 g (0.1 mol) crystallized methyl-n-octadecyl-diallylammonium bromide through heating with tap water and cooling to 30°–35° C. in order to prevent recrystallization of the ammonium salt. The prepared solutions are then added, drop by drop, from two dripping funnels during the course of 40 minutes under vigorous stirring and simultaneous introduction of air oxygen, wherein care should be taken that the temperature of the reaction mixture does not fall below 30° C. The sulfobetaine starts already to crystallize upon dripping of the solutions from the reaction mixture as a snow-white substance. The pH value of the reaction mixture is kept at 7 during the entire dripping phase. After a post-reaction time of approximately 10 minutes, the sulfobetaine is suctioned off from the reaction mixture and dried. The yield is nearly quantitative. The recrystallization from ethanol confirms that the raw sulfobetaine accumulates practically free from neutral salts. Melting point 165° C. The product exhibits the following $^{13}C$-NMR spectrum in $DMSO_{D6}$ (indications as above).

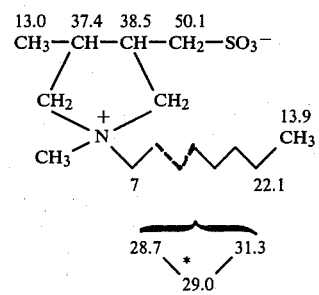

\* most intensive peak
peaks not attributed: 41.6; 40.6; 39.5.

We claim:

1. A sulfobetaine compound of the following formula I

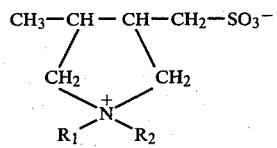

wherein $R_1$ is hydrogen, straight-chained or branched alkyl groups of one to 22 carbon atoms or benzyl, $R_2$ is straight-chained or branched alkyl groups of 1 to 22 carbon atoms, and $R_1$ and $R_2$ may be the same or different.

2. The compound of claim 1 wherein $R_1$ and $R_2$ are —$CH_3$.

3. The compound of claim 1 wherein $R_1$ is —$CH_3$ and $R_2$ is hydrogen.

4. The compound of claim 1 wherein $R_1$ is $C_6H_5CH_2$— and $R_2$ is hydrogen.

5. The compound of claim 1 wherein $R_1$ is —$CH_3$ and $R_2$ is —$C_8H_{17}$.

6. The compound of claim 1 wherein $R_1$ is —$CH_3$, and $R_2=$—$C_{10}H_{21}$.

7. The compound of claim 1 wherein $R_1$ is —$CH_3$, and $R_2$ is —$C_{12}H_{25}$.

8. The compound of claim 1 wherein $R_1$ is —$CH_3$ and $R_2=$—$C_{14}H_{29}$.

9. The compound of claim 1 wherein $R_1$ is —$CH_3$ and $R_2$ is —$C_{16}H_{33}$.

10. The compound of claim 1 wherein $R_1$ is —$CH_3$ and $R_2$ is —$C_{18}H_{37}$.